US006548545B1

(12) United States Patent
Thompson

(10) Patent No.: US 6,548,545 B1
(45) Date of Patent: *Apr. 15, 2003

(54) TREATMENT OF INTERSTITIAL CYSTITIS USING TOPICAL APPLICATION OF MENTHOL AND L-ARGININE

(75) Inventor: Ronald J. Thompson, Ft. Thomas, KY (US)

(73) Assignee: 40 J's LLC, Fort Thomas, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/968,055

(22) Filed: Oct. 1, 2001

(51) Int. Cl.[7] .................. A61K 31/195; A61K 31/045
(52) U.S. Cl. ........................ 514/565; 514/729
(58) Field of Search ................. 514/565, 729

(56) References Cited

U.S. PATENT DOCUMENTS 5,085,854 A * 2/1992 Faukuda et al. ............ 424/63
5,837,735 A   11/1998 Miyata et al.
5,877,216 A   3/1999 Place et al.
5,895,658 A   4/1999 Fossel
6,007,824 A   12/1999 Duckett et al.
6,139,873 A   10/2000 Hughes, Jr. et al.
6,143,300 A * 11/2000 Stevenot ................ 424/195.1

OTHER PUBLICATIONS

Medline 99112654, Korting, et al, J. Urol. Feb., 1999 161(2) 559–65, abstract.*

* cited by examiner

*Primary Examiner*—Rebecca Cook
(74) *Attorney, Agent, or Firm*—Don Halgren

(57) ABSTRACT

A topical treatment for interstitial cystitis in the urinary tract of a mammal comprising an ointment including a component of L-Arginine in a carrier base compound. The ointment may also include a component of menthol. The concentration of menthol and of L-Arginine is each preferably limited to five percent.

3 Claims, No Drawings

TREATMENT OF INTERSTITIAL CYSTITIS USING TOPICAL APPLICATION OF MENTHOL AND L-ARGININE

BACKGROUND OF THE INVENTION

1. Field of the Invention

This invention relates to a method to utilize a topical preparation of menthol and L-arginine as a therapeutic modality for interstitial cystitis, which is otherwise known as "overactive bladder".

2. Prior Art

The function of the urinary bladder is to accumulate a significant volume of urine before the sensation of bladder fullness, and the need to urinate, is perceived. This is a bodily function most of us take for granted. The normal volume of urine before bladder fullness is appreciated is 300 to 400 cc. Frequency is a patient-reported symptom of frequent urination. In the absence of either excessive fluid intake or the therapeutic use of diuretics, urination should be necessary only every 4 to 6 hours.

Cystitis is an inflammation of the bladder commonly caused by a bacterial infection in the urine and the superficial bladder wall. Symptoms associated with cystitis are frequent urination (frequency), pelvic pressure, dysuria (painful urination) and nocturia (the need to urinate that interrupts normal sleep). The diagnosis of bacterial cystitis is established by the identification of the presence of white blood cells upon microscopic examination of the urine. Effective treatment of a bacterial cystitis is accomplished with oral antibiotics.

Interstitial cystitis is a widespread disease of women who have the symptoms of a bacterial cystitis—frequency, pelvic pressure and nocturia—but in the absence of a urinary tract infection. In the June 2001 *Journal of Urology* Abstract #43, Dr. Perelman reports in "The Cost to Diagnose Interstitial Cystitis" that the typical interstitial cystitis patient has symptoms for 2–7 years and sees multiple physicians prior to diagnosis. Current treatments available for interstitial cystitis, once the diagnosis is established, include the anticholinergic and antimuscarinic agents oxybutynin chloride and tolterodine tartrate. These agents are widely advertised for "overactive bladder" in direct-to-consumer advertising designed to refer patients to physicians with the statement, "Ask your doctor." Both Detrol LA® (tolterodine tartrate), and Ditropan XL® (oxybutynin chloride), are oral systemic anticholinergic therapies designed to decrease the overall muscle (detrussor) tone—but with very troublesome side effects. These systemic side effects include drowsiness, blurred vision, fever and heat stroke due to decreased sweating, dry mouth, constipation, headache, and dyspepsia.

Anatomy of the Lower Urinary Tract System

The lower urinary tract system in females includes the urethra, trigone, and urinary bladder. The female urethra is a muscular tube about 3.0 to 4.0 centimeters in length that proximally ends at the external urethral meatus and distally terminates in the urinary bladder cavity at the trigone. The trigone is the stationary base of the bladder that does not move as the bladder fills with urine: it contains the proximal urethral orifices, right and left, as well as the terminus of the distal urethra. All of the vasculature and nerves that supply the entire distensible blabber are located in the region of the trigone. This allows the bladder to fill with urine, but without the distortion of the vesicular vessels or nerves. Anatomically, the trigone and urethra are located just above the vaginal mucosa and endopelvic fascia in the dorsal aspect of the vagina. The urinary bladder (vesicle) is an intraperitoneal muscular organ and therefore can progressively distend (cephalad) as the bladder progressively fills with urine. The bladder muscle is also referred to as the detrussor muscle or simply as the detrussor.

The detrussor muscle is a vessel-like muscle fashioned like an inverted drawstring purse. The detrussor is composed of smooth muscle. Smooth muscle has the unique property that it can be gradually actively stretched without evoking a muscle contraction. This stretching of the detrussor is referred to as compliance. Interstitial cystitis is thought of as the loss of detrussor compliance and a small bladder capacity.

Urodynamic testing is accomplished by first passing a small tube through the urethra and into the bladder and completely emptying the bladder of urine. This small tube is then used to infuse water into the bladder at a very gradual rate of 100 cc/minute. The normal initial sense of bladder fullness should be reported when the bladder has 250 to 300 cc of water. If the patient reports the symptoms of bladder fullness at 100 cc of urine and pressure/pain symptoms at 150 cc of urine, the diagnosis of interstitial cystitis is fairly assured, in the absence of a bladder infection. This symptom represents lack of compliance. A denovo bladder contraction occurring at a low volume of water is a diagnostic of urge (the urge to urinate) incontinence, another symptom in hyperactive or overactive bladder.

The decreased or loss of detrussor compliance can be explained by one of three interrelated functions. The loss of normal detrussor muscle function, the loss of normal sensory nerve function within the bladder, or the loss ot adequate vascularization (oxygen supply by the arteries and arterioles) necessary for the normal functioning of the muscle and nerves. In her NIH-sponsored research reported in the December 1997 *Jounal of Urology,* Dr. Wheeler's article, "Effect of Long-Term Oral L-arginine on the Nitric Oxide Synthase Pathway in the Urine from Patients with Interstitial Cystitis," concludes:

Oral L-arginine treatment increases nitric oxide synthase activity, induces nitric oxide synthase immunoreactivity, and cGMP and nitrate plus nitrite levels in the urine of patients with interstitial cystitis. These biochemical changes are associated with a decrease in interstitial cystitis related symptoms including urinary frequency and pain. (703)

Also in her report, Dr. Wheeler identifies three isoforms of the nitric oxide synthase enzyme: neuronal (NUOS), endothelial (eNOS-endothelial cells line arteries and artrioles), and inducible NOS (presumably contained in the detrussor muscle itself). The inducible NOS was found to be increased with oral therapy with 1500 mg of L-arginine per day; after 2–6 months of therapy, the patients reported improved symptoms of interstitial cystitis. As the only substrate for the NOS pathway, the presence of a substrate load with L-arginine therapy seems to induce the NOS to produce elevated, therapeutically successful levels of nitric oxide and cGMP.

The theoretical question, "Could a local topical preparation of menthol and L-arginine be successful in the treatment of interstitial cystitis without the noxious systemic symptoms of the anticholinergic therapies?" In May, 2001, a situation involving a 53 year-old woman on an anticholingeric agent for treatment of her "overactive bladder" was reviewed. This woman patient had been using a topical menthol/L-arginine product described in U.S. Pat. No. x,yyy,zzz to enhance her sexual responsiveness. This menthol/L-arginine preparation had been applied to the vestibular tissue, including the clitoris and the external urethral meatus for three weeks on about an every-other-day basis. Because of travel problems, she had exhausted her supply of anticholingeric therapy (Detrol®), but, to her surprise, her symptoms of interstitial cystitis did not reemerge. With continuous use of the topical menthol/L-arginine preparation, the patient has remained off of anticholingeric therapy and is symptom-free from interstitial cystitis. These findings are explainable in light of the cited references, all reporting improved symptoms of interstitial cystitis on L-arginine oral systemic administration and the postulates of L-arginine inducible nitric oxide synthase activity:

1. Wheeler, M. A., Smith, S., Saito, N., Foster, H. E., Jr. and Weiss, R. M.: Effect of long-term oral L-arginine on the nitric oxide synthase pathway in the urine from patients with interstitial cystitis. J. Urol., 158: 2045, 1997.
2. Smith, S. D., Wheeler, M. A., Foster, H. E., Jr. and Weiss, R. M.: Improvement in interstitial cystitis symptom scores during treatment with oral L-arginine. J. Urol., 158: 703, 1997.
3. Chung, B. H., Choi, S. K. and Chang, K. C.: Effects of nitric oxide on detrussor relaxation. J. Urol., 155: 2090, 1996.
4. Monacada, S. and Higgs, E. A.: Molecular mechanisms and therapeutic strategies related to nitric oxide. F.A.S.E.B. J., 9:1319, 1995.
5. Smith, S. D., Wheeler, M. A., Foster, H. E., Jr. and Weiss, R. M.: Urinary nitric oxide synthase activity and cGMP levels are decreased with interstitial cystitis and increased urinary tract infections. J. Urol., 155: 1432, 1996.
6. Wheeler, M. A., Pontari, M., Dokita, S., Nishimoto, T., Cho, Y. H., Hong, K. W. and Weiss, R. M.: Age-dependent changes in particulate and soluble guanylyl cylase activities in urinary tract smooth muscle. Mol. Cell. Biochem., 169:115, 1997.

BRIEF SUMMARY OF THE INVENTION

The present invention relates to a treatment for interstitial cystitis. The treatment involves a preparation of menthol and L-arginine as a therapeutic modality to treat such interstitial cystitis (overactive bladder) in a first embodiment, by topical delivery to the vestibular tissues, including the external urethral meatus as a cream or ointment. Such a cream has a composition of menthol in a concentration of less than five percent (5%), and L-arginine in a concentration of less than five percent (5%), in a carrier. The cream compound in this first embodiment would be applied to the vestibular tissues, including the urethral meatus by use of manual application of such cream or ointment by the patient or doctor. Such application of this cream or ointment would be topically applied to the patient continuously over an extended period of time for proper treatment of interstitial cystitis.

A second embodiment uses a compound of menthol and L-arginine which is applied topically to the urethra and trigone as an intraurethral suppository. The menthol in this compound has a concentration range of five percent (5%) or less and the L-arginine has a concentration range of five percent (5%) or less. The intraurethral suppository compound may be. is applied as cocoa butter and is inserted onto the urethra and trigone by the patient or doctor. Similarly, the application of this cream or ointment would be topically applied to the patient continuously over an extended period of time for proper treatment of interstitial cystitis A third embodiment intends the utilization of a compound of menthol and L-argine in a strength of five percent (5%) or less menthol and five percent (5%) or less L-Arginine applied topically to the urethra/trigone/bladder neck transvaginally with a vaginal suppository (the vagina lacks sensory fibers and therefore a higher concentration of menthol is possible than in embodiments 1 and 2 described hereinabove). The application of this cream or ointment would also be topically applied to the patient continuously over an extended period of time for proper treatment of interstitial cystitis A fourth embodiment comprises a compound applied topically in a solution infuse into the bladder, to topically apply to the urothelial cells and to diffuse directly into the detrussor. Such a solution comprises five percent (5%) or less menthol, and five percent (5%) or less L-argine. It is applied by use of a catheter inserted into the bladder with or without the use of a cystoscope. The application of the cream or ointment of this embodiment of the present invention would preferably be applied on a weekly basis for up to several months.

A fifth embodiment comprises a topically applied compound in a solution as in the fourth embodiment described hereinabove, but infused at the time of cystoscopy as an in-office treatment. Such a cystoscopic treatment comprises pretreatment or initial treatment for one or multiple treatments and then with continuing therapy with a topical cream or ointment. The application of the cream or ointment of this embodiment of the present invention would also be preferably applied to the patient on a daily basis for a continuous control of the symptoms of overactive bladder.

The invention thus is a topical treatment for interstitial cystitis comprising an ointment including a component of L-Arginine in a carrier base compound. The ointment may include a component of menthol. The component of L-Arginine is preferably in a concentration of less than five percent in the compound. The component of menthol is preferably in a concentration of less than five percent in the compound.

The invention also includes a method of treating interstitial cystitis of the lower urinary tract in mammals comprising the steps of preparing a topical ointment of L-Arginine in a carrier compound and applying the topical ointment of L-Arginine to a portion of the lower urinary tract of a mammal. The steps may include limiting the topical ointment of L-Arginine in the carrier compound to a concentration of five percent, adding menthol as an ingredient to the topical ointment of L-Arginine in the carrier compound, limiting the ingredient of menthol in the carrier compound to a concentration of five percent. The steps of the invention may also include preparing a intraurethral suppository to include the carrier compound; and introducing the intraurethral suppository to the urethra and trigone of the lower urinary tract of a mammal to provide a topical application of the ointment and carrier compound thereto for the treatment of interstitial cystitis.

The invention method of treating interstitial cystitis may also include the steps of preparing a vaginal suppository to include the ointment in the carrier compound; and introducing the vaginal suppository to the urethra, trigone and bladder neck of the lower urinary tract of a mammal to provide a topical application of the ointment in the carrier compound thereto for the treatment of interstitial cystitis; preparing the ointment as a solution for infusion into the bladder; and infusing the solution into the bladder of the lower urinary tract of a mammal to provide a topical application of the ointment to the urothelial cells and to diffuse directly into the detrussor for the treatment of interstitial cystitis.

The method of treating interstitial cystitis may include preparing the ointment as a solution for infusion into the bladder; and introducing the solution to the urethra and trigone of the lower urinary tract of a mammal during a cystoscopic procedure therewith, to provide a topical application of the ointment thereto for the treatment of interstitial cystitis.

I claim:

1. A method of treating interstitial cystitis of the lower urinary tract in a mammal in need thereof comprising:

administering a composition comprising effective amounts of L-arginine and menthol to treat interstitial cystitus, whereby the composition is a topical ointment, a suppository or a solution for infusion into the bladder.

2. The method of treating interstitial cystitis as recited in claim 1, wherein said amount of L-Arginine in said carrier compound is a concentration of no greater than five percent.

3. The method of treating interstitial cystitis as recited in claim 1, wherein said ingredient of menthol in said carrier compound is a concentration of no greater than five percent.

* * * * *